(12) United States Patent
Tomlinson

(10) Patent No.: US 10,143,584 B1
(45) Date of Patent: Dec. 4, 2018

(54) SPLINT KIT SET

(71) Applicant: Robert J. Tomlinson, Springdale, AR (US)

(72) Inventor: Robert J. Tomlinson, Springdale, AR (US)

(73) Assignee: READYSPLINTS L.L.C., Springdale, AR (US)

( * ) Notice: Subject to any disclaimer, the term of this patent is extended or adjusted under 35 U.S.C. 154(b) by 831 days.

(21) Appl. No.: 14/447,252

(22) Filed: Jul. 30, 2014

(51) Int. Cl.
*A61F 5/00* (2006.01)
*A61F 5/058* (2006.01)

(52) U.S. Cl.
CPC .... *A61F 5/05866* (2013.01); *A61F 2210/008* (2013.01); *A61F 2250/0062* (2013.01)

(58) Field of Classification Search
CPC ........ A61F 5/01; A61F 5/058; A61F 5/05866; A61F 5/05841; A61F 5/05875; A61F 2250/0062
USPC ................................................ 206/440, 441
See application file for complete search history.

(56) References Cited

U.S. PATENT DOCUMENTS

| | | | | |
|---|---|---|---|---|
| 5,284,468 A | * | 2/1994 | Nelson | A61F 5/05825 602/5 |
| 5,480,376 A | * | 1/1996 | Duback | A41D 13/015 428/68 |
| 7,921,999 B1 | * | 4/2011 | Kimball | A61F 13/00063 206/440 |
| 8,771,209 B2 | * | 7/2014 | Evans | A61F 13/00072 206/440 |

* cited by examiner

*Primary Examiner* — Kim M Lewis
(74) *Attorney, Agent, or Firm* — Schrantz Law Firm, PLLC; Stephen D. Schrantz

(57) ABSTRACT

The splint kit provides a sealed splint, bandaging, and a water source for setting the splint. Different kits may be needed depending upon the size of the user to which the splint will be applied. The kits may also vary according to the body part to be set. The size of each splint is based upon the size of the user and the size of the body part(s) to be splinted to eliminate the need for the user to size the splint. The splint is self-contained in its own packaging to maintain the integrity of the splint. The fiberglass/hardening material is encased by a foam material and/or felt to further simplify the process of applying and setting the splint.

6 Claims, 24 Drawing Sheets

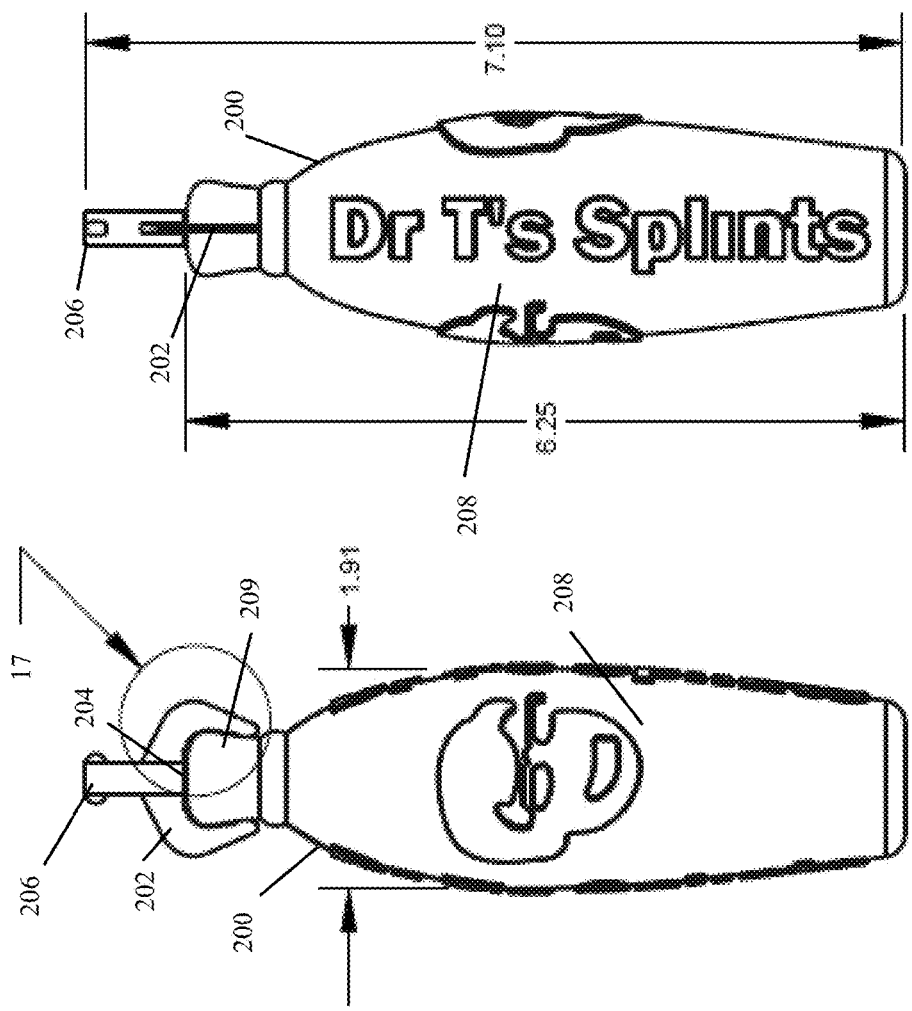

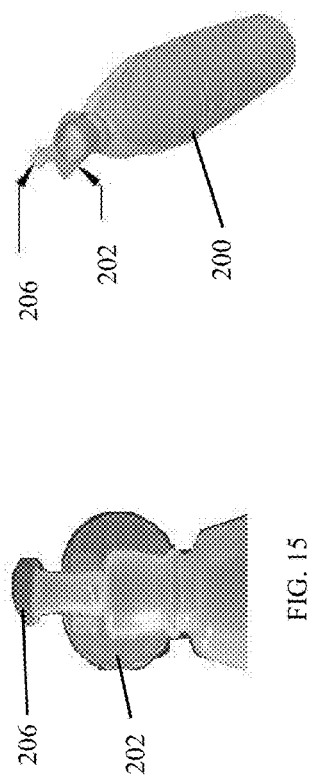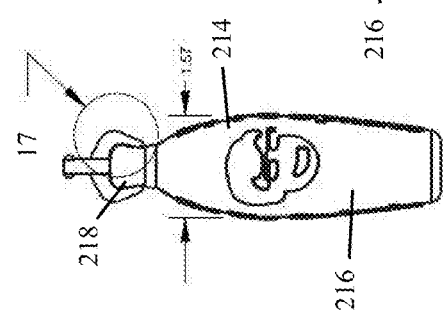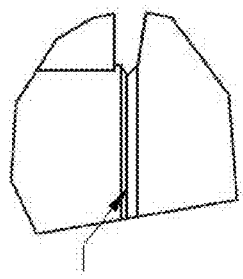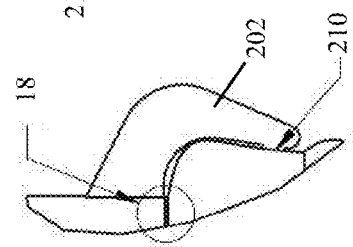

SPLINT KIT SET

CROSS-REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

RESERVATION OF RIGHTS

A portion of the disclosure of this patent document contains material which is subject to intellectual property rights such as but not limited to copyright, trademark, and/or trade dress protection. The owner has no objection to the facsimile reproduction by anyone of the patent document or the patent disclosure as it appears in the Patent and Trademark Office patent files or records but otherwise reserves all rights whatsoever.

BACKGROUND OF THE INVENTION

I. Field of the Invention

This invention relates generally to a splint for treating injuries to a user. The present invention is designed to be applied in a hospital, doctor's office, or in the field. The present invention provides the user with the necessary materials to splint a user.

II. Description of the Known Art

The present invention relates generally to the field of orthopedic medicine and more specifically to a splint kit. Splints are used in treating and transporting patients who have suffered a bone or joint injury, such as a fracture or dislocation. The task of the splint is to stabilize the broken or fractured body parts quickly and with minimal pain and discomfort to the patient.

Splints are typically rigid supports made of various substances, such as plaster, fiberglass, plastic, metal, or inflatable materials, which temporarily support an injured extremity. Splints may be held in place by an elastic bandage, hook and loop, or other wrapping. Splints generally do not rigidly encircle a limb to allow for swelling in the early stages of an injury. Typically, splints are applied in an emergency setting. Several components are required and considerable skill is necessary to apply a splint.

Patents and patent applications disclosing relevant information are disclosed below. These patents and patent applications are hereby expressly incorporated by reference in their entirety.

U.S. Pat. No. 7,960,603 issued to Evans on Jun. 14, 2011 ("the '603 patent") teaches a medical bandage that includes a knitted spacer fabric cover or padding positioned in surrounding relation on a moisture-hardenable substrate. A reactive system taught by the '603 patent is applied to and into the thickness of the substrate. The reactive system taught by the '603 patent having a first state wherein the substrate remains in a flexible, conformable condition and a second state wherein the reactive system hardens, simultaneously hardening the substrate into a desired conformation.

U.S. Pat. No. 7,172,565 issued to Termanini on Feb. 6, 2007 ("the '565 patent") teaches a water-curable orthopedic splint, which can be immediately applied to an affected limb includes a water-curable orthopedic casting material, which is in the form of a splint, and a gel container. The word gel is meant to apply to a viscous semi-solid which can be applied over surfaces in an adherent film and will disperse and move in response to the movement of the practitioner's hands in molding and forming the adhesive bandage around the limb or in the formation of various shapes as splints prior to application to the patient. It is to be distinguished from a free-flowing liquid which drips when applied to a limb resulting in a messy environment.

U.S. Pat. No. 6,482,167 issued to Grim, et al. on Nov. 19, 2002 ("the 167 patent") teaches a technique for forming orthopaedic splints or supports that includes the steps of impregnating the edges of casting material with non-rigid bonding material and subsequently impregnating the casting material with water hardenable material such as urethane. The edge treatment taught by the '167 patent keeps the edges in a relatively cushioning or non-rigid state to avoid irritation of the skin of the patient. The blanks taught by the '167 patent may be formed using a mold having a groove defining the outline of the casting blank, and a ridge for implementing the impregnation of a bead of bonding material into the casting fabric. The casting blank material taught by the '167 patent may be formed of spacer or double knit type material, or may be formed of several layers of fabric including high strength filaments, and may have padding material as one layer.

U.S. Pat. No. 7,465,283 issued to Grim, et al. on Dec. 16, 2008 ("the '283 patent") teaches a cast or support assembly that includes inner double knit padding material in which the outer layer is woven or knit to have substantial size openings, while the inner layer of the double knit material to be located against the skin of the patient is more closely woven or knit. The '283 patent teaches that additional casting fabric is also provided, with this casting fabric being impregnated with water hardenable material. The outer casting fabric taught by the '283 patent may include openings extending through it, so that the entire cast assembly has ventilation openings allowing air circulation to accomplish rapid drying following wetting of the assembly by sweat, rain, or by swimming, for example.

U.S. Pat. No. 7,972,288 issued to Chabba, et al. on Jul. 5, 2011 ("the '288 patent") teaches a medical bandaging product, including a sleeve formed of moisture-impervious material and sealable to prevent entry of moisture, and a medical material positioned in the sleeve and sealed therein against entry of moisture until use. The medical material taught by the '288 patent is a substrate having two marginal areas of relatively lower modulus yarns and/or a more open knitted structure to provide reduced abrasion against the skin. A reactive system on the substrate taught by the '288 patent remains stable when maintained in substantially moisture-free conditions and hardens upon exposure to sufficient moisture to form a rigid, self supporting structure. The '288 patent teaches that a soft, flexible protective material covers at least one of the major faces of the substrate along its length to provide a cushioning barrier between the substrate and the skin of a patient when the material is in use.

U.S. Pat. No. 7,004,917 issued to Henderson, et al. on Feb. 28, 2006 ("the '917 patent") teaches hardenable orthopaedic supports and methods of making the same. One embodiment taught by the '917 patent provides a support which includes a blank made of a permeable, flexible material and including a structural region impregnated with a hardenable material and a peripheral region which will remain flexible after the hardenable material is hardened. Another embodiment taught by the '917 patent provides a method of manufacturing an orthopaedic support in which a permeable, flexible material is positioned adjacent a recess of a molding element; the flexible material is contacted with a hardenable material; and the hardenable material is placed under pressure in the molding element to impregnate the section of the flexible material with the hardenable material.

SUMMARY OF THE INVENTION

Splinting of an injured limb or joint is a basic first aid technique to provide immobilization and comfort, to prevent further injury, and to minimize swelling. The current state of the art splinting performed in the family practitioner's office, the orthopedic surgeon's office, or the emergency room involves the use of a multi-ply fiberglass sheet cut from a continuous roll covered by foam material/felt. The rolls come in widths from 2 to 5 inches, usually 15 feet in length enclosed in a box. The fiberglass roll is enclosed in an air tight envelope to maintain its pliability. After cutting a portion of the fiberglass roll, the user must reseal the envelope using a plastic clip. Each cut of the roll exposes the hardening material/fiberglass found within the foam material/felt. The exposure of the hardening material/fiberglass increases the difficulty of applying the splint as the caregiver may need gloves to apply the splint.

The length of the splint to be cut is either estimated based on the body part to be splinted or measured from the limb to be splinted and then cut. The length is often times estimated as the splint is usually doubled back at the ends to prevent the sharp edge and rough fiberglass from irritating the limb. The splinting technique varies greatly due to the training differences in the caregiver applying the splint. The splint may be applied by a physician, a nurse, a medical assistant, or medical personnel. There is a general consensus that there is a proper and uniform method for splinting of the wrist, elbow, knee, and ankle to provide maximum comfort and protection of the limb.

The present invention provides a concise and uniform methodology for splinting of the wrist, elbow, ankle, and knee independent of the caregiver applying the splint. Therefore, the splint kit of the present invention can be utilized both at home, in the professional medical setting, at an athletic event, on the field, on the court, or outdoors. Early and appropriate splinting provides immediate first aid, comfort, piece of mind, and allows flexibility in treatment options. In some cases, early treatment may preclude the need for "emergency care". In the medical setting, the splint kits of the present invention provide safe, uniform, concise, convenient, and efficient splinting without waste.

The present invention relates generally to a splint kit that provides the user with all of the materials and equipment required to apply and set a splint. More specifically, the splint kit provides a sealed splint, bandaging, and a water source for setting the splint. Different kits may be needed depending upon the size of the user to which the splint will be applied. The kits may also vary according to the body part to be set. Sizing the splint based upon the size of the user and the size of the body part(s) to be splinted eliminates the need for the user to size the splint. The splint kit of the present invention provides the user with a mobile splint kit that may be applied in many different environments.

The splint is self-contained in its own packaging to maintain the integrity of the splint. As the splint is exposed to moisture, including moisture in the air, the splint may be activated to harden. The packaged splint eliminates contact of the splint with moisture. The splint sealed within the package is sized to be used in a single use. The user will use the entire splint such that little to no excess splint will remain. Therefore, the unused portions of the splint will not be required to be sealed and stored.

Traditional splints are available in roll form packaged within a sealable package. The user cuts the amount of splint material needed from the roll. The user then reseals the roll within the package. The packaging does not fully seal the roll. The roll is then exposed to moisture and begins to harden prior to use of the roll.

Furthermore, the roll of splint material is formed from a material that is difficult to cut. Traditional splints material therefore require a special type of scissors for cutting and sizing the splint. The splints of the present invention are sized for a specific use. These single use sized splints of the present invention eliminate requiring the user to size the splint. The user also does not require the specialized scissors for sizing the splint. Furthermore, the sealed splint material designed for single use does not require resealing the packaging. The splint material is thus not activated allowing the splint material not to be wasted.

One embodiment of the present invention provides a precut enclosed splint, which may be sewn. The enclosed splint provides a more comfortable experience for the user. The enclosed splint also assists the caregiver applying the splint as the rough edges of the splint are covered. Therefore, the caregiver may avoid wearing gloves when applying and setting the splint.

Water or another substance is usually applied to the splint to activate the splint. As the splint is activated, the splint begins to harden. The user then applies the splint to the injured area to stabilize the area.

The treating user may then apply a bandage to secure the splint to the user. The bandage is packaged in the splint kit. The applied splint then stabilizes the injury thus reducing pain and further injury.

It is an object of the present invention to provide a user with all the necessary material to apply a splint.

It is an object of the present invention to maintain the integrity of the splint material.

It is an object of the present invention to seal the splint to prevent moisture from activating the splint.

It is an object of the present invention to size the splint to enable a user to easily apply a splint.

It is an object of the present invention to eliminate the need for a user to manually size the splint.

It is an object of the present invention to provide a sealed water source to be applied to the splint.

It is an object of the present invention to provide a container for a water source that does not require a special tool for opening the water source.

It is an object of the present invention to supply all of the materials needed to apply and set a splint.

It is an object of the present invention to provide a precut enclosed splint available in the appropriate length for the body part to be splinted.

It is an object of the present invention to provide the number of splints needed for each particular body part.

It is an object of the present invention to be sized depending upon the person who will be wearing the splint.

It is an object of the present invention to provide an enclosed splint in which the ends of the splint are enclosed.

It is an object of the present invention to allow a caregiver to avoid wearing gloves when applying and setting the splints.

It is an object of the present invention to provide visual instructions on the packaging to assist with educating and facilitating the ease of applying the splint.

It is an object of the present invention to provide a portable solution for applying a splint.

It is an object of the present invention to provide a sized splint with exposed ends to reduce manufacturing costs.

It is an object of the present invention to provide a splint that may be applied anywhere.

It is an object of the present invention to provide flexibility in treatment options.

It is an object of the present invention to increase safety by improving immobilization of the user.

These and other objects and advantages of the present invention, along with features of novelty appurtenant thereto, will appear or become apparent by reviewing the following detailed description of the invention.

BRIEF DESCRIPTION OF THE DRAWINGS

In the following drawings, which form a part of the specification and which are to be construed in conjunction therewith, and in which like reference numerals have been employed throughout wherever possible to indicate like parts in the various views:

FIG. 13 is a front view of a water source housing of one embodiment of the present invention, the rear view being a mirror image of the front view;

FIG. 14 is a right side view thereof, the left side view being a mirror image of the right side view;

FIG. 15 is a partial view of a water housing of one embodiment of the present invention;

FIG. 16 is a perspective view thereof;

FIG. 17 is a partial view thereof;

FIG. 18 is a partial view thereof;

FIG. 19 is a front view thereof, the rear view being a mirror image of the front view;

FIG. 20 is a right side view thereof, the left side view being a mirror image of the right side view;

DETAILED DESCRIPTION

Figure 1:
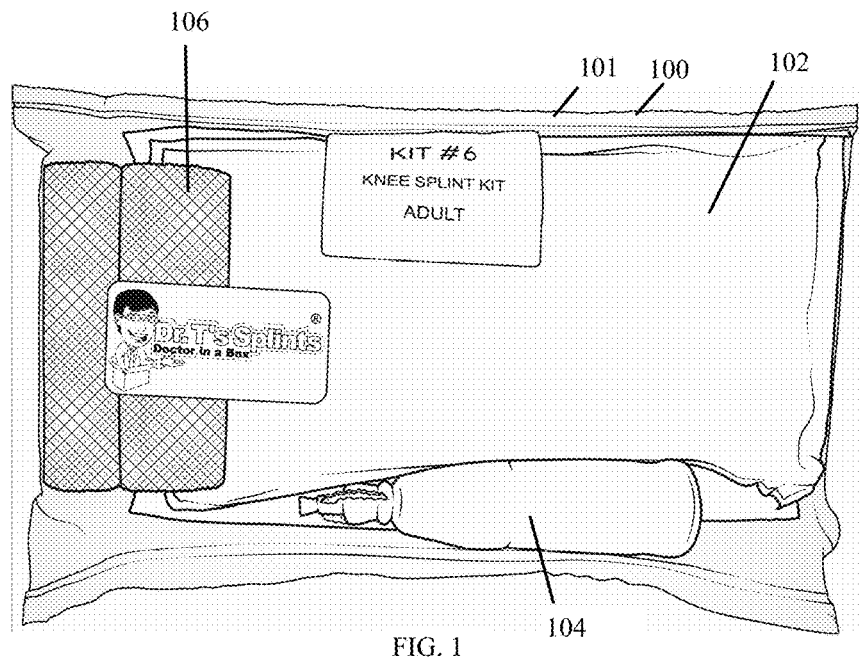
FIG. 1 is a front view of one embodiment of the present invention.

The present invention relates generally to a splint kit 100 shown in FIGS. 1-4 that provides the user with all of the materials and equipment required to apply and set a splint. The splint kit 100 of the present invention provides the user with a mobile splint kit that may be applied in many different environments. The materials needed to apply and set the splint are packaged in a first housing 101, such as a packaging. More specifically, the splint kit 100 provides a sealed splint 102, bandaging 106, and a water source 104 for setting the splint. Different kits may be needed depending upon the size of the user to which the splint will be applied. The kits may also vary according to the body part to be set with the splint kit. The sized splints eliminate the need for the user to size the splint. Therefore, the sized splint allows the user to apply and set the splint without cutting or otherwise adjusting the size of the splint.

The number of splints packaged within a housing may also vary according to the body part to be set. For example, the wrist splint kit and forearm kit may be packaged with one splint. The ankle splint kit, elbow splint kit, and knee kit, on the other hand, may be packaged with two splints, wherein each splint may vary in width and/or length. Each kit provides the appropriate number of splints required to stabilize the injured body part.

Figure 2:
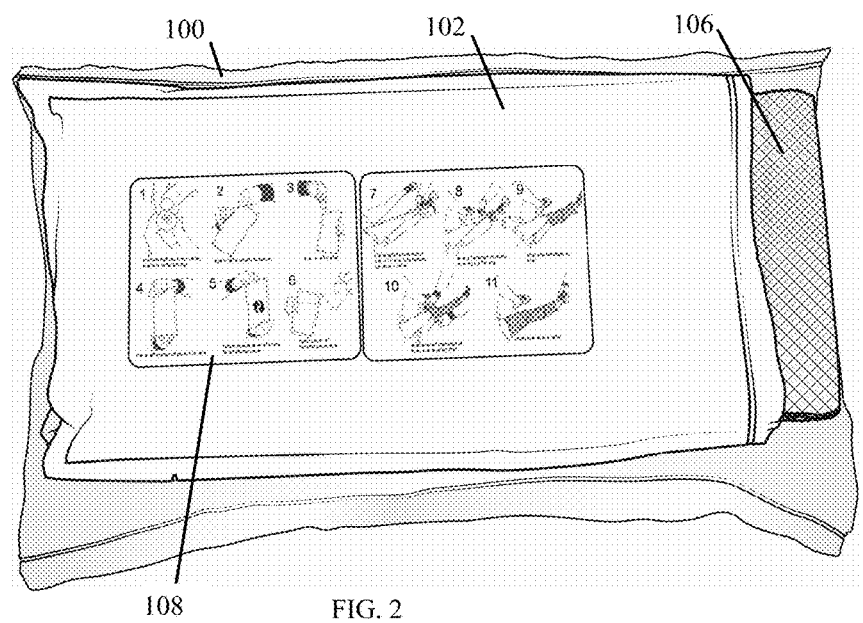
FIG. 2 is a rear view thereof.
Figure 3:
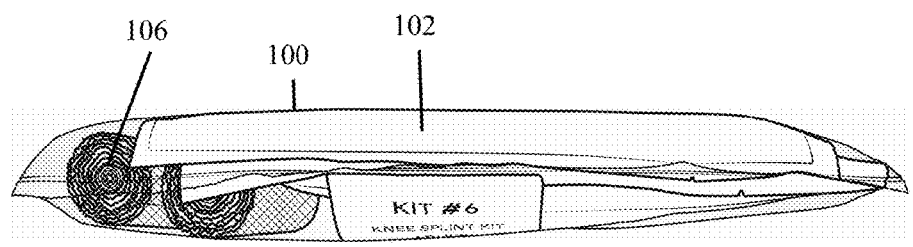
FIG. 3 is a top view thereof.
Figure 4:
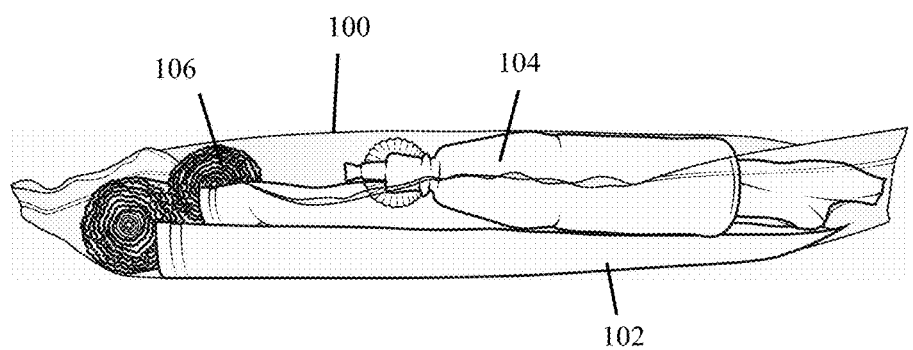
FIG. 4 is a bottom view thereof.

FIG. 2 shows the back side of the splint kit 100. The kit 100 provides a set of instructions 108 informing the user the method to apply and set the splint. The instructions 108 may also provide drawings such as those shown in the figures showing the proper method in to apply and set the splint.

Figure 5:
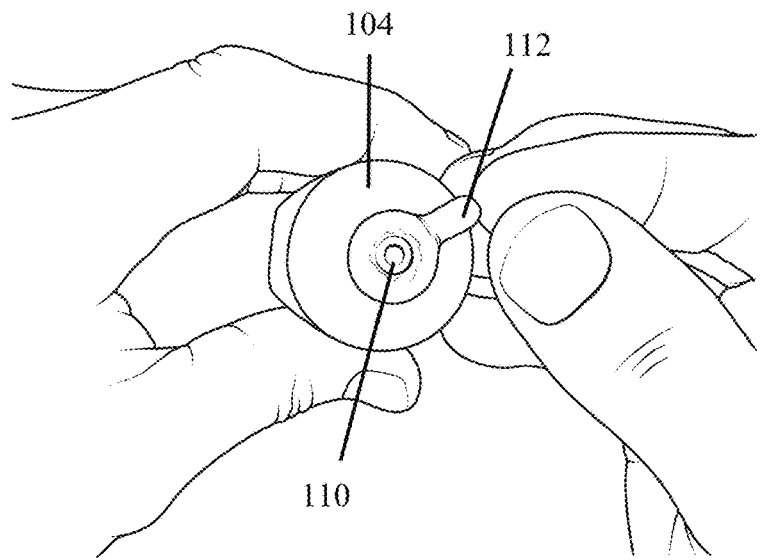
FIG. 5 is an environmental top view of a water source housing of one embodiment of the present invention.

FIG. 5 shows a water source 104 of one embodiment of the present invention. The water source 104 stores water to be used in applying the splint. The housing of the water source 104 includes a release finger 112 located on top 110 that enables the user to open top 110 of the water source 104 to apply the water. Removal of the top 110 creates an opening from which the water may flow. Once open, the user may apply the water to the splint to activate the splint. In one embodiment, the splint is stored within a second housing.

The water from the water source is placed into the second housing for application to the splint as will be described below.

Figure 6:
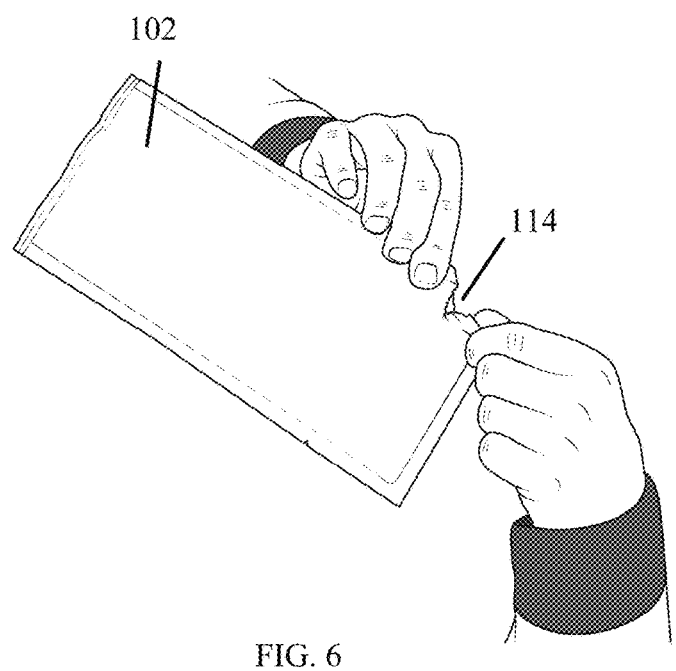
FIG. 6 is an environmental view of a splint housing of one embodiment of the present invention.

FIG. 6 shows the splint housing 102 that seals the splint. The splint is stored in a moisture-tight housing 102 that limits the splint's contact with moisture. The splint is self-contained in its own packaging to maintain the integrity of the splint. As the splint is exposed to moisture, including moisture in the air, the splint is activated and begins to harden. The packaged splint stored within housing 102 eliminates contact of the splint with moisture. The splint sealed within the housing 102 is sized to be used in a single use. The user will use the entire splint such that little to no excess splint will remain. Therefore, the unused portions of the splint will not be required to be sealed and stored.

Figure 8:
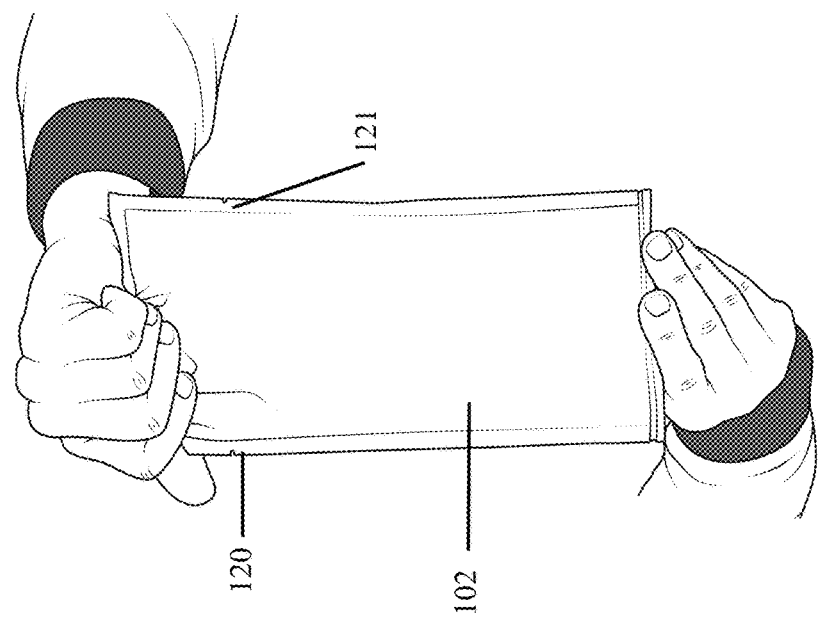
FIG. 8 is an environmental view thereof.
Figure 7:
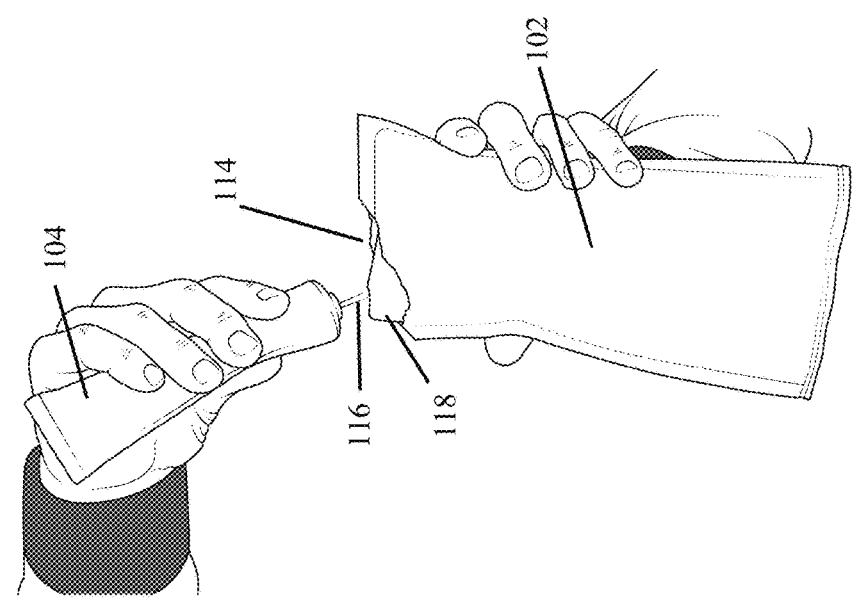
FIG. 7 is an environmental view of one embodiment of the present invention.
Figure 10:
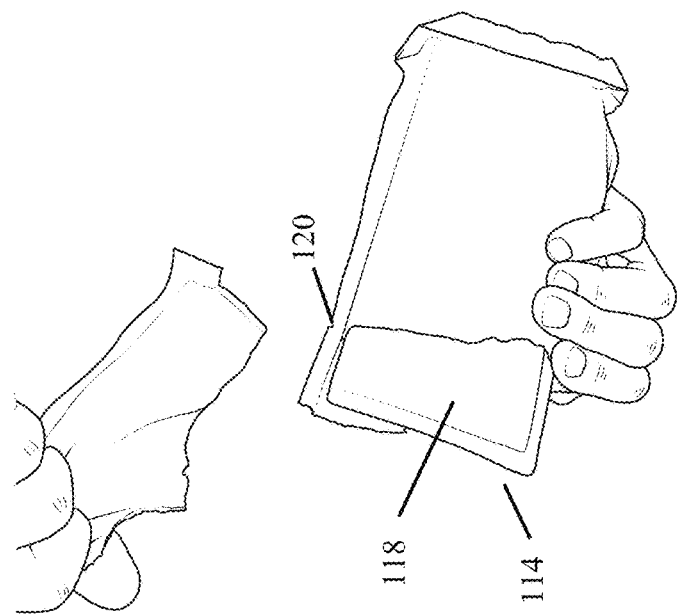
FIG. 10 is an environmental view thereof.
Figure 9:
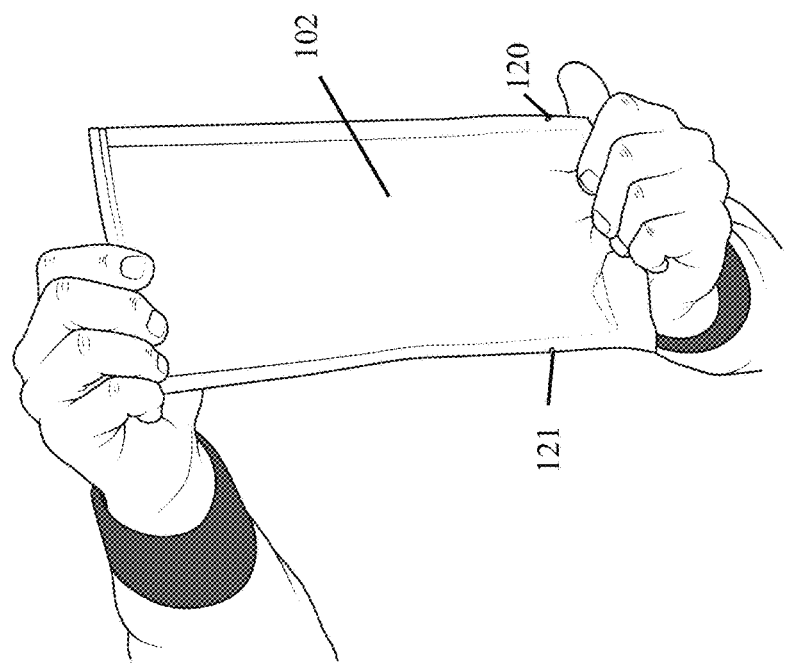
FIG. 9 is an environmental view thereof.

The user creates an opening 114 of the splint housing 102 at opening notch 120, 121. The splint housing 102 provides two opening notches 120, 121 to provide the user with two opportunities to create an opening. The user may open the splint housing 102 at the first opening notch 120 to create opening 114 as shown in FIG. 7. The user then applies water 116 from water container 104 into opening 114. The water 116 contacts splint 118 to activate the splint 118. As shown in FIGS. 8 and 9, the user then folds the splint housing 102 onto itself to at least partially close the splint housing 102. The user may then agitate the housing 102 to disburse the water through the housing 102. The agitation of the housing 102 enables enough water to be applied throughout the splint 118 to activate the splint 118. After the water has been applied throughout the splint 118, the user may fully open the housing 102 to remove the splint 118 as shown in FIG. 10.

Figure 11:
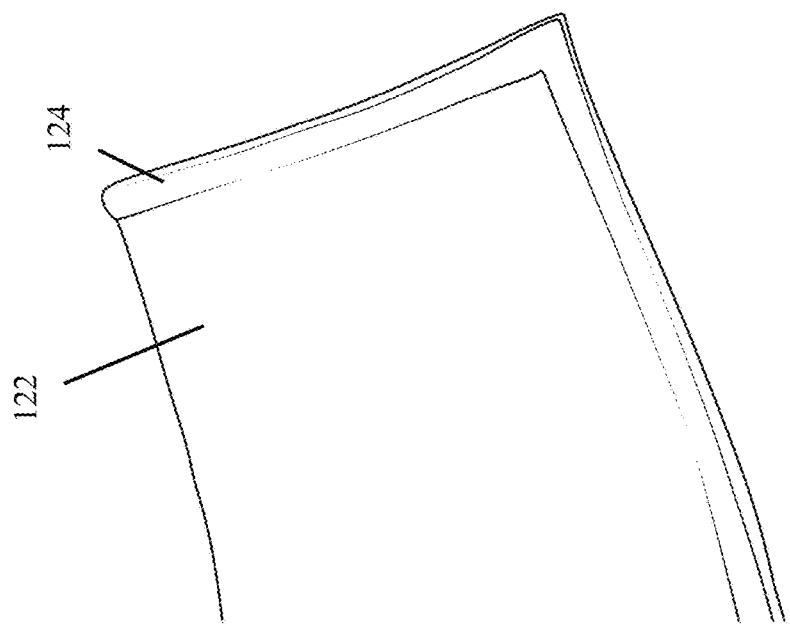
FIG. 11 is a partial view of a splint of one embodiment of the present invention.
Figure 22:
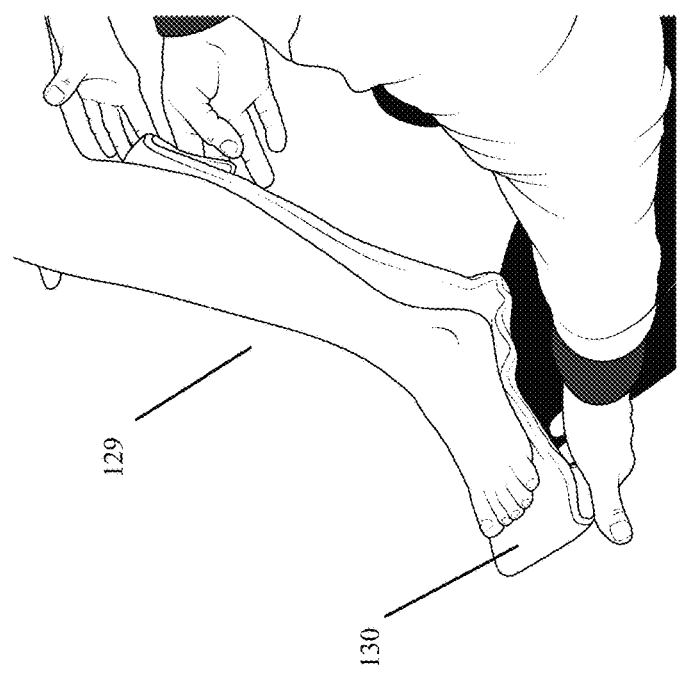
FIG. 22 is an environmental view of one embodiment of the present invention.

The splints of the present invention are available in two different configurations. Each splint may be constructed from fiberglass or other hardening material. The fiberglass is encased in foam material/felt. The splint may have closed ends 124 as shown on splint 122 in FIG. 11. The closed ends 124 of splint 122 eliminate exposed fiberglass. The fiberglass may be a rough and scratchy surface that could irritate a user's skin. The felt encloses the fiberglass thus limiting exposure of the fiberglass. The closed ends 124 limit contact with the fiberglass such that the user will not be irritated by the fiberglass. In one embodiment, the splint 122 has closed ends 124 due to the end being sewn. The ends may be closed by other known methods. The closed ends 124 of splint 122 may also reduce the equipment needed to apply and set splint 122. The caregiver may avoid using gloves when applying splint 122 due to the closed ends 124 encasing the fiberglass.

Figure 12:
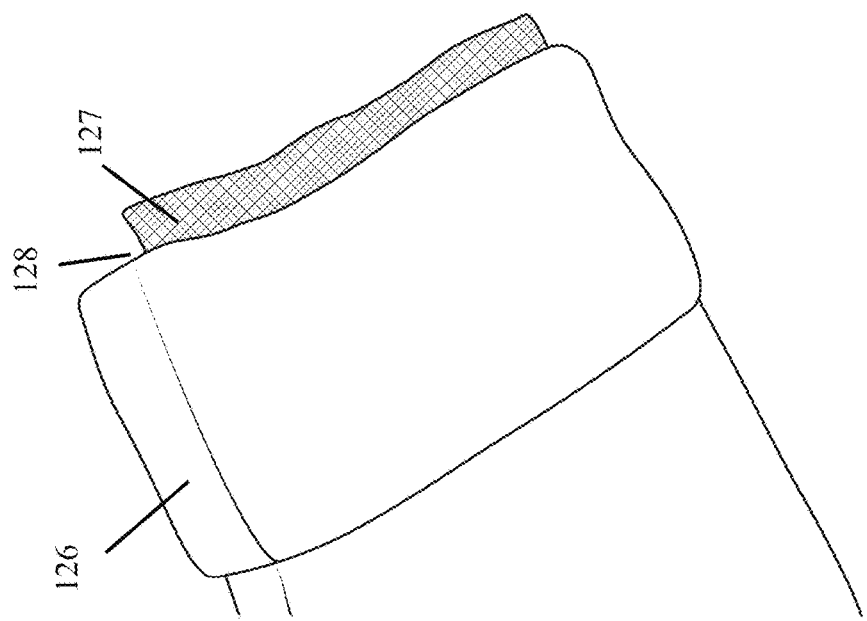
FIG. 12 is a partial view of a splint of one embodiment of the present invention.

FIG. 12 shows a different embodiment of the splint 126 in which the foam material/felt does not completely enclose the fiberglass 127. Instead, splint 126 provides an open end 128 at each end. Fiberglass 127 is exposed in such a splint 126 with an open end 128. To eliminate contact of the rough edge of the open end 128 of the splint with the user, the person applying the splint rolls the edge backwards onto the splint to avoid contact of the open end 128 with the user.

FIGS. 13-20 show a fluid/gel source of the present invention wherein the fluid activates the fiberglass/hardening material. In one embodiment, the container 200 stores water. The container 200 provides a head 206 and shoulder 202 that seal the container 200 at opening 204. The head 206 and shoulder 202 releasably attach to container 200 to allow the user to remove the shoulder 202 and head 206 to access opening 204. Removal of head 206 and shoulder 202 allows water to flow from body 208 through opening 204. Sufficient water must be packaged within each kit so that the appropriate amount of water may be applied to the splint for activation. In one embodiment, the present invention may provide either a six ounce bottle or a three ounce bottle storing the water.

FIGS. 13-14 show one embodiment of the six ounce water source. The height of container 200 from body 208 to neck 209 ranges from 3 to 9 inches, preferably 6.25 inches. The width of container 200 ranges from 0.5 inch to 4 inches, preferably 1.91 inches.

FIGS. 13 and 15-18 provide more detailed information regarding the head 206 and neck 209. As described above, head 206 and shoulder 202 releasably attach to containers 200, 214 to seal the containers 200, 214. The head 206 secures to the neck 209 at attachment 212. The shoulder 202 secures to the neck 209 at attachment 210. Attachment 210, 212 enables the user to remove head 206 and shoulder 202 from the containers 200, 214 to access opening 204.

FIGS. 19 and 20 show one embodiment of the three ounce water source. The height of container 214 from body 216 to neck 218 ranges from 3 to 9 inches, preferably 5.83 inches. The width of container 200 ranges from 0.5 inch to 4 inches, preferably 1.57 inches.

Figure 21:
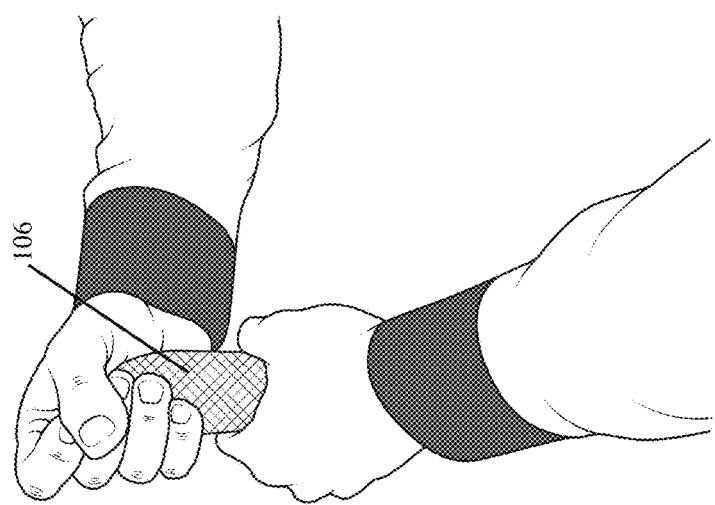
FIG. 21 is an environmental view of one embodiment of the present invention.
Figure 24:
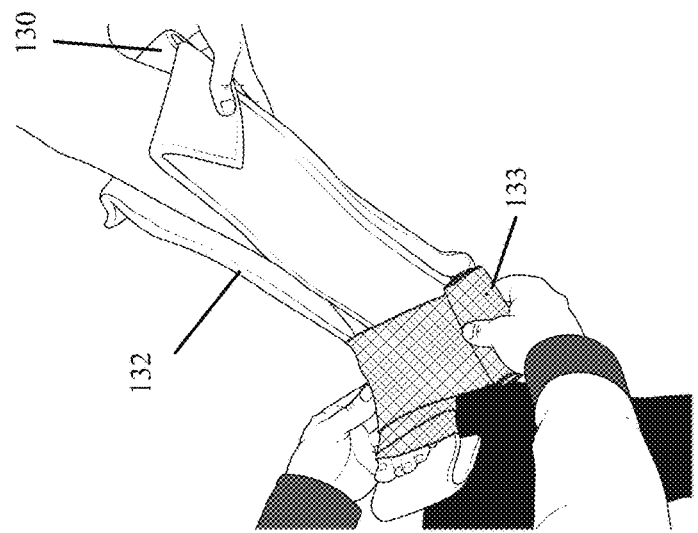
FIG. 24 is an environmental view thereof.
Figure 23:
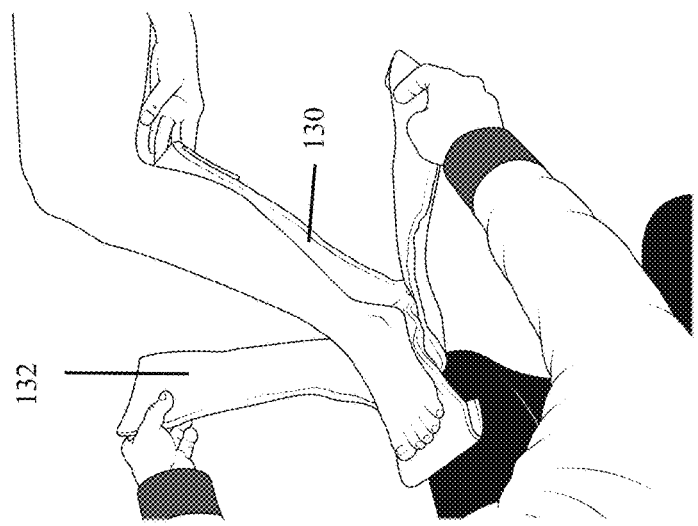
FIG. 23 is an environmental view thereof.
Figure 26:
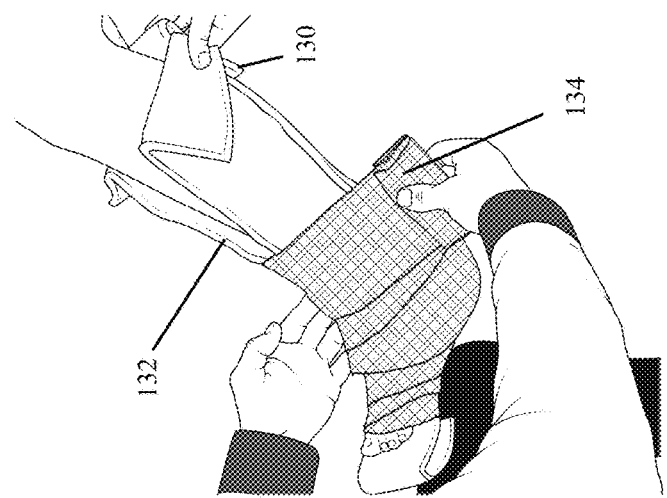
FIG. 26 is an environmental view thereof.
Figure 25:
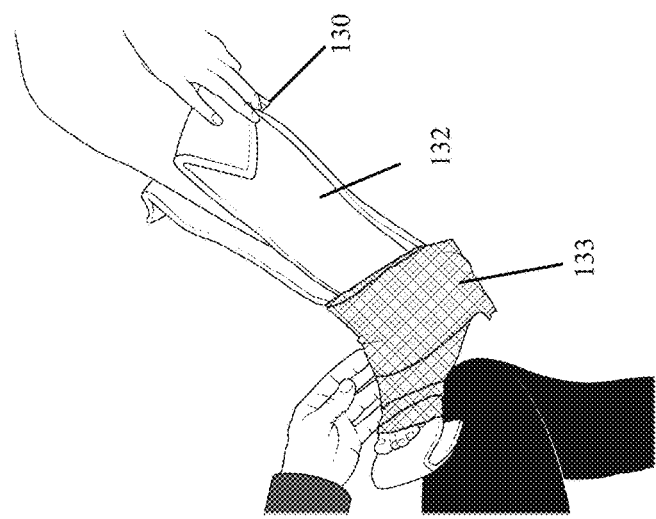
FIG. 25 is an environmental view thereof.
Figure 27:
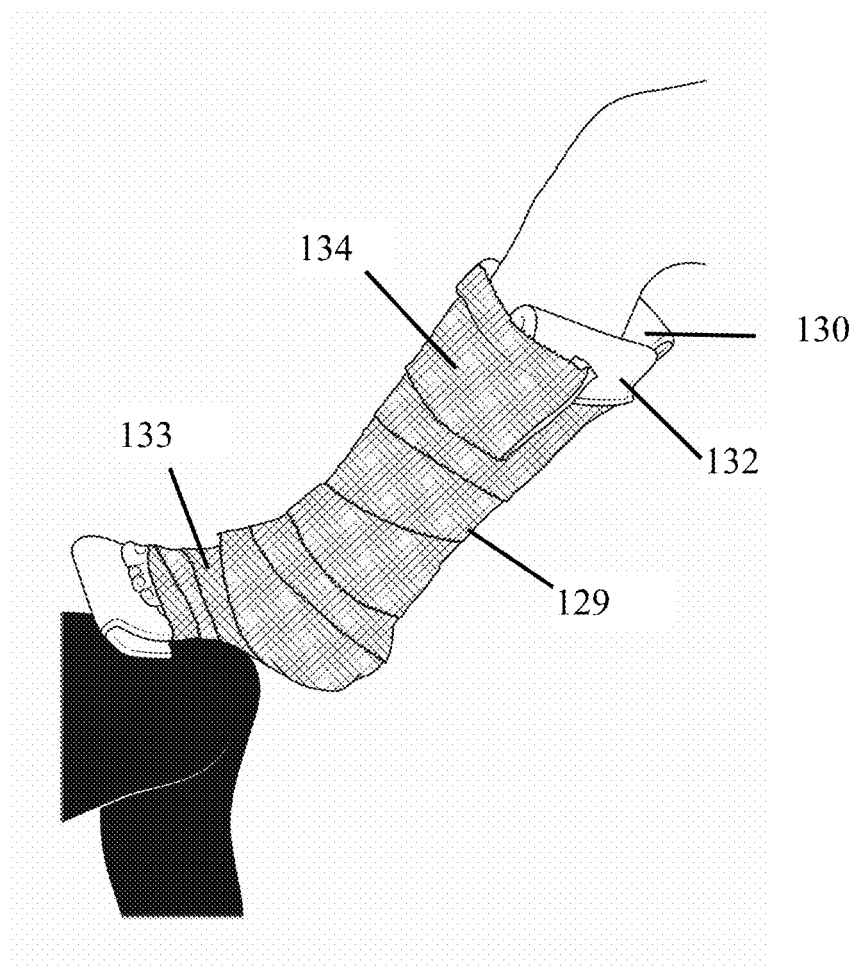
FIG. 27 is an environmental view thereof.
Figure 28:
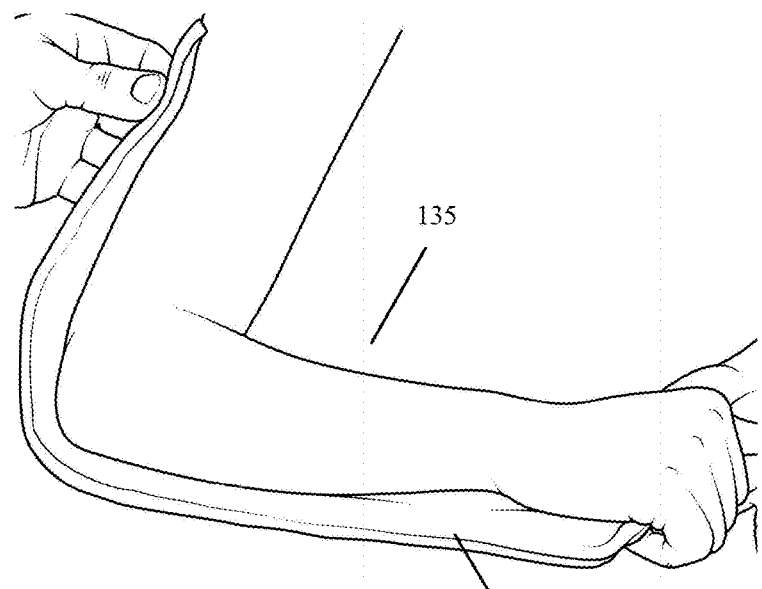
FIG. 28 is an environmental view of one embodiment of the present invention.
Figure 29:
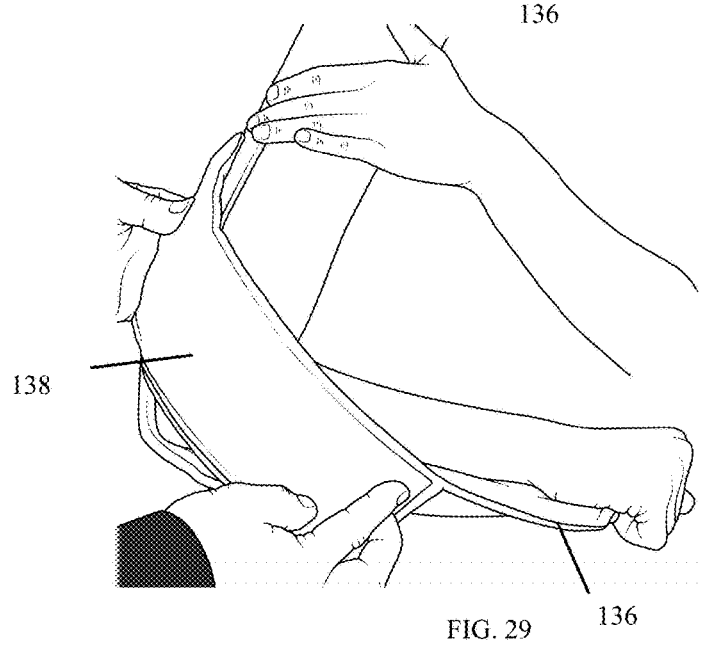
FIG. 29 is an environmental view thereof.
Figure 30:
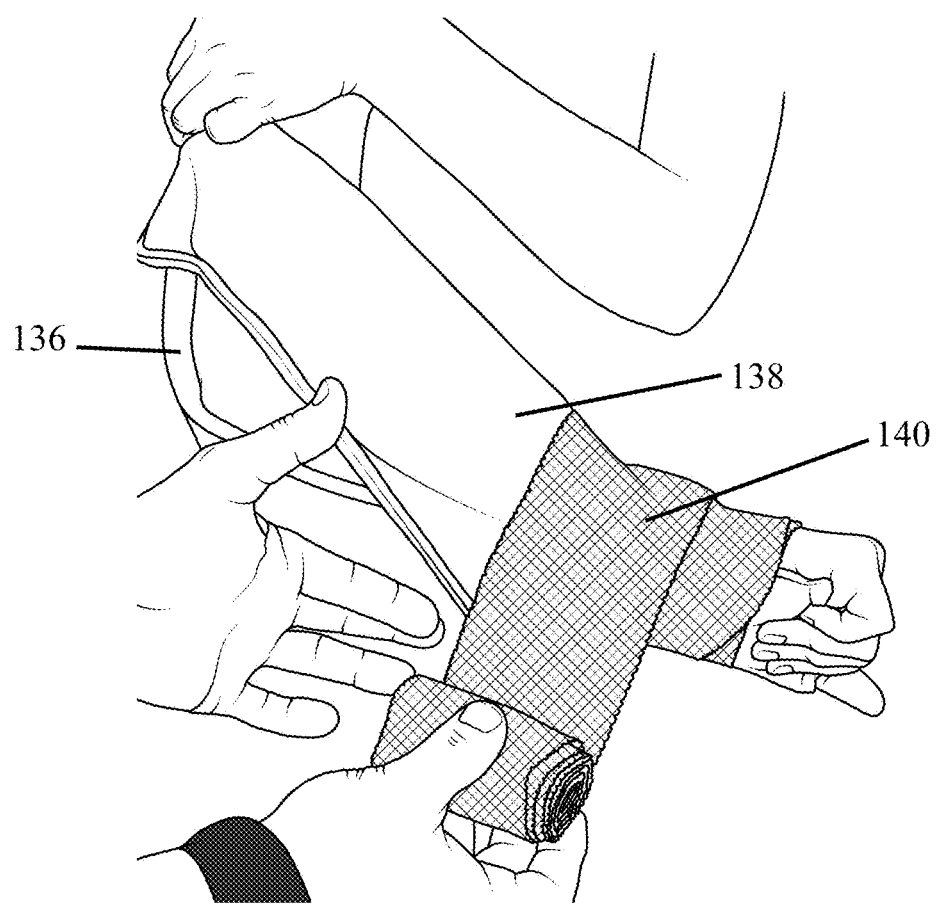
FIG. 30 is an environmental view thereof.
Figure 32:
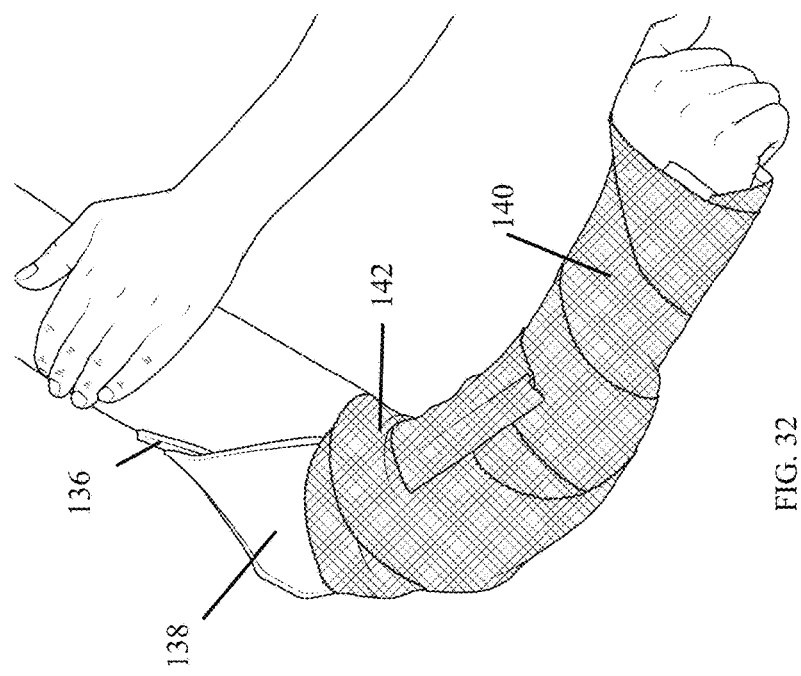
FIG. 32 is an environmental view thereof.
Figure 31:
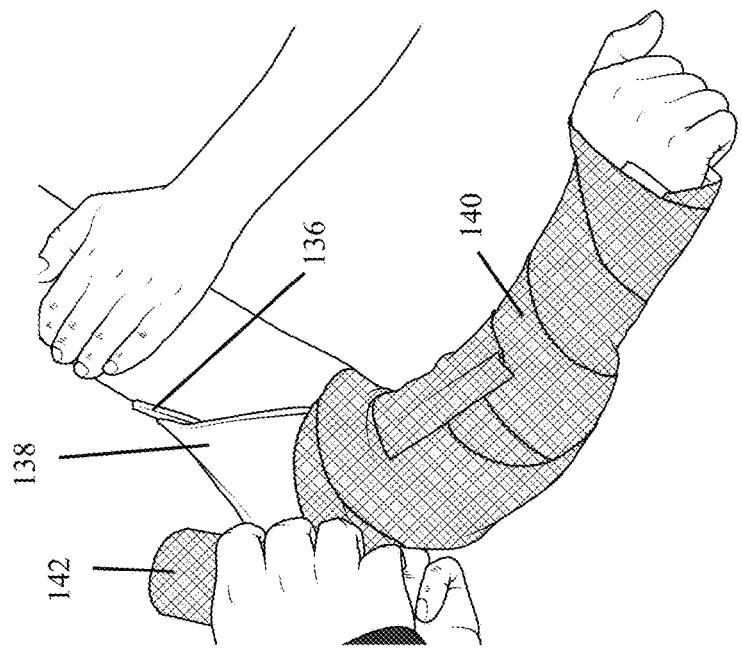
FIG. 31 is an environmental view thereof.
Figure 33:
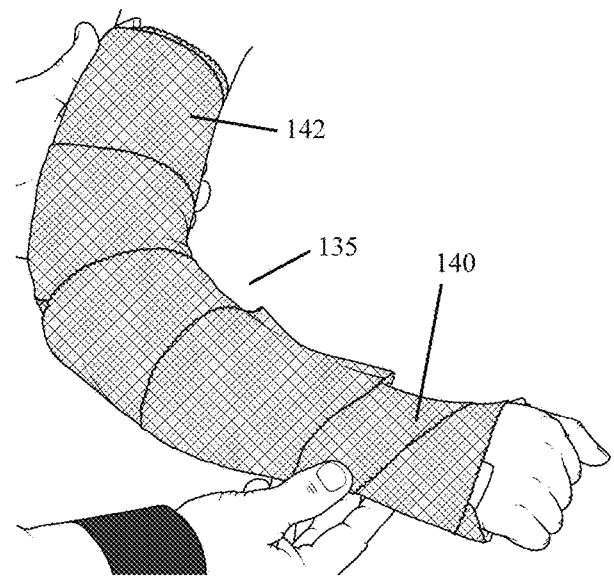
FIG. 33 is an environmental view thereof.

FIG. 21 shows the bandage 106 that is applied to the splint to secure the splint to the user. The bandage 106 of one embodiment has elastic qualities that enable the bandage 106 to secure the splint to the user. The bandage 106 is wrapped around the user and the splint to secure the splint and stabilize the body part. The bandage 106 is supplied in an appropriate length to secure the splint to the user. Therefore, the user is not required to cut the bandage 106 to properly size the bandage. The caregiver applies bandage 106 to secure the splint to the user. The applied splint then stabilizes the injury thus reducing pain and further injury.

FIGS. 22-27 show the splints 130, 132 and bandage 133, 134 available in an ankle splint kit 129. The ankle splint kit 129 provides a first splint 130 and a second splint 132. The ankle splint kit 129 also provides a first bandage 133 and a second bandage 134. The ankle splint kit 129 is available in both a child size and an adult size.

The splints 130, 132 of the child size ankle kit ranges from two (2) inches wide to five (5) inches wide, preferably three (3) inches wide. The length of the first splint 130 may range from ten (10) inches to forty (40) inches, preferably twenty (20) inches. The length of the second splint 132 may range from ten (10) inches to forty (40) inches, preferably thirty (30) inches. The bandages 133, 134 of the child size ankle kit range from two (2) to ten (10) inches in width, preferably four (4) inches.

The splints 130, 132 of the adult size ankle kit range from two (2) inches wide to six (6) inches wide, preferably four (4) inches wide. The length of the first splint 130 may range from ten (10) inches to forty five (45) inches, preferably thirty (30) inches. The length of the second splint 132 may range from ten (10) inches to fifty (50) inches, preferably thirty-six (36) inches. The bandages 133, 134 of the adult size ankle kit range from two (2) to twelve (12) inches in width, preferably six (6) inches.

FIGS. 22-27 also show the instructions for applying the ankle splint kit 129. These instructions may be provided on the housing 101 at instructions 108. FIGS. 22-27 show the placement of the splints 130, 132 on the leg and ankle of the user for setting the splint.

FIGS. 28-33 show the splints 136, 138 and bandages 140, 142 of elbow splint kit 135. The elbow splint kit 135 provides a first splint 136 and a second splint 138. The elbow splint kit 135 also provides a first bandage 140 and a second bandage 142. The ankle splint kit 135 is available in both a child size and an adult size.

The splints 136, 138 of the child size elbow kit range from two (2) inches wide to five (5) inches wide, preferably three (3) inches wide. The length of the first splint 136 may range from ten (10) inches to thirty (30) inches, preferably 16 inches. The length of the second splint 138 may range from five (5) inches to twenty (20) inches, preferably ten (10) inches. The bandages 140, 142 of the child size elbow kit range from one (1) to eight (8) inches in width, preferably three (3) inches.

The splints 136, 138 of the adult size elbow kit range from two (2) inches wide to six (6) inches wide, preferably three (3) inches wide. The length of the first splint 136 may range from five (5) inches to thirty (30) inches, preferably twenty (20) inches. The length of the second splint 138 may range from five (5) inches to twenty (20) inches, preferably thirty-six (36) inches. The bandages 140, 142 of the adult size elbow kit range from two (2) to ten (10) inches in width, preferably four (4) inches.

FIGS. 28-33 also show the instructions for applying the elbow splint kit 135. These instructions may be provided on the housing 101 at instructions 108. FIGS. 28-33 show the placement of the splints 136, 138 on the arm and elbow of the user for setting the splint.

Figure 34:
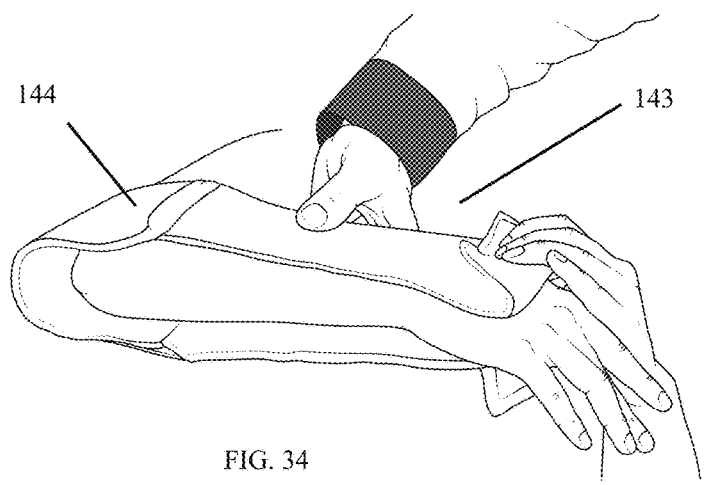
FIG. 34 is an environmental view of one embodiment of the present invention.
Figure 35:
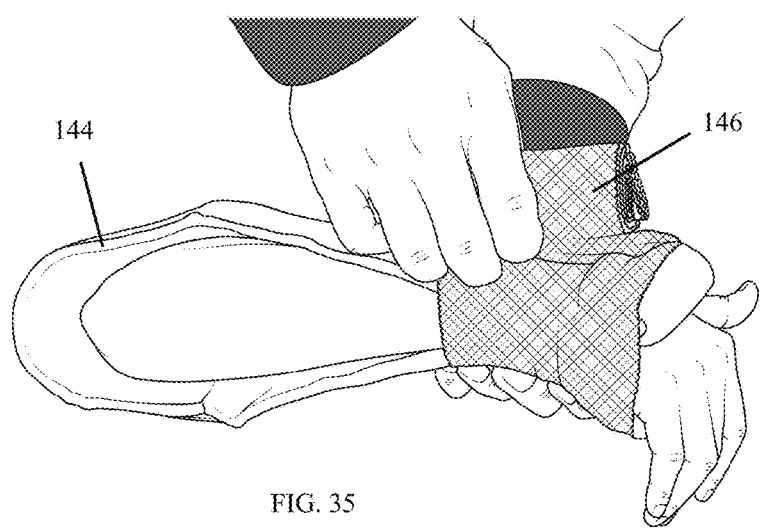
FIG. 35 is an environmental view thereof.
Figure 36:
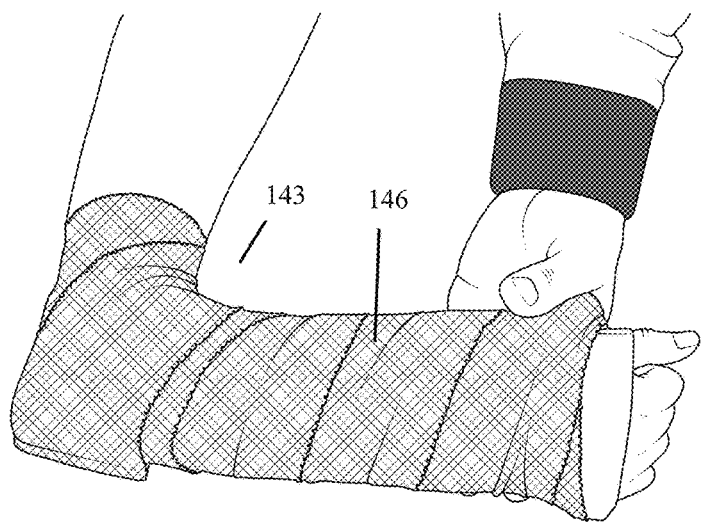
FIG. 36 is an environmental view thereof.
Figure 37:
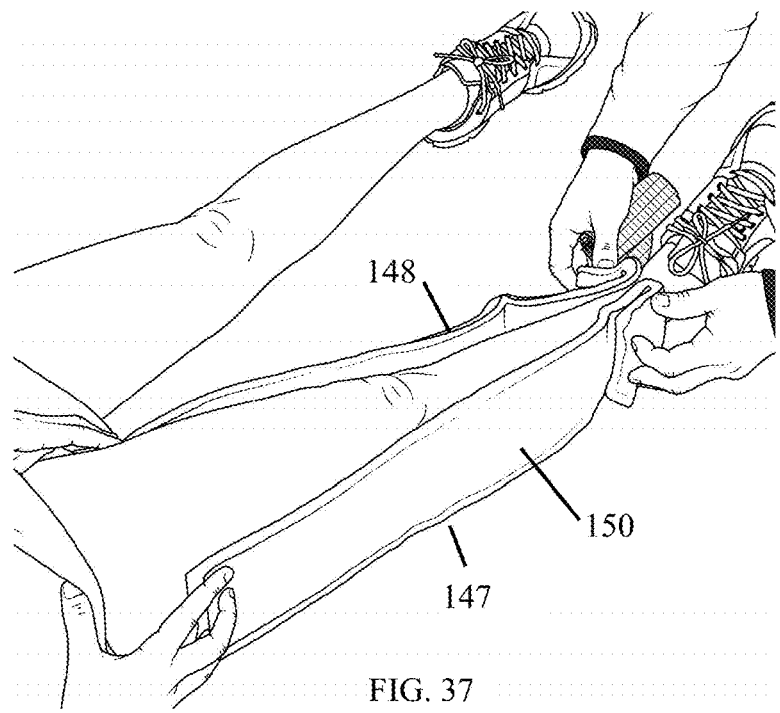
FIG. 37 is an environmental view of one embodiment of the present invention.
Figure 38:
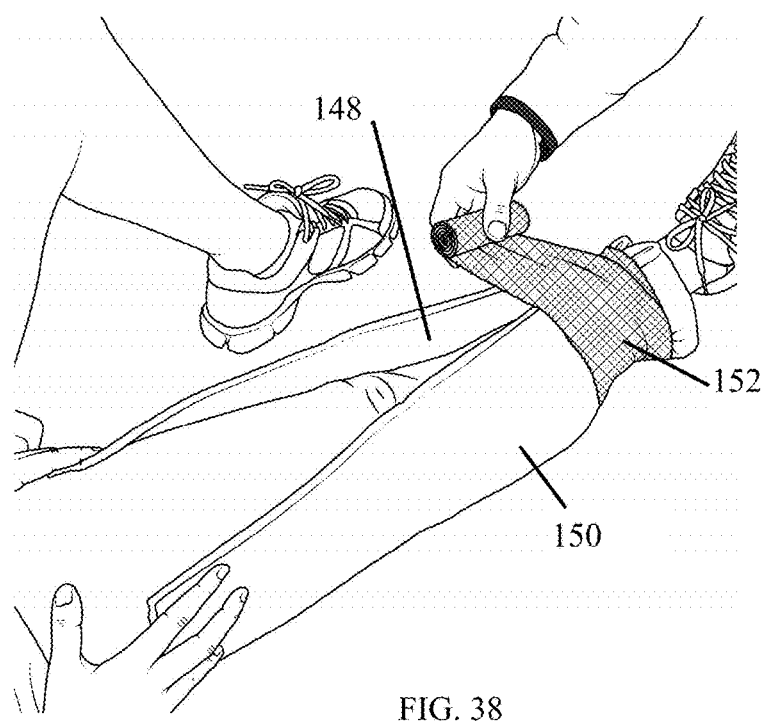
FIG. 38 is an environmental view thereof.
Figure 39:
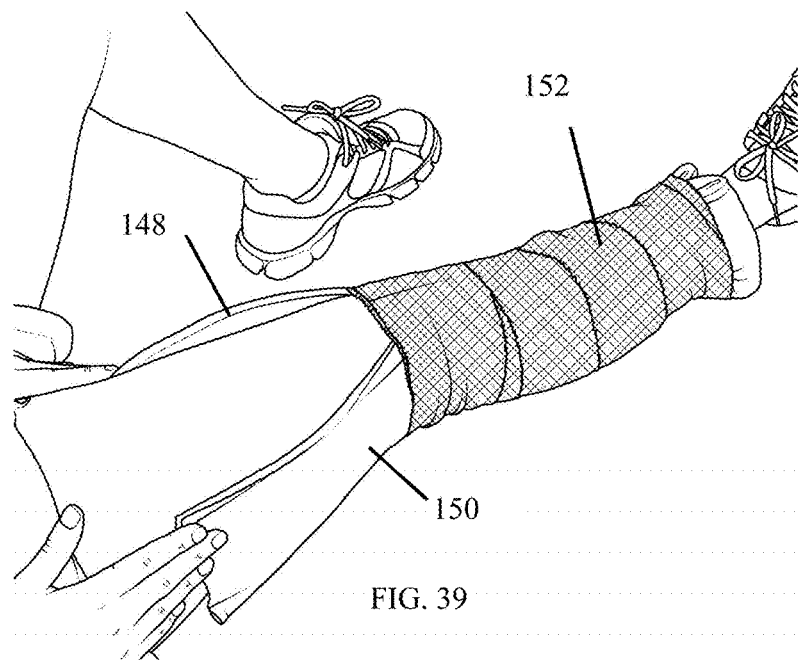
FIG. 39 is an environmental view thereof.
Figure 40:
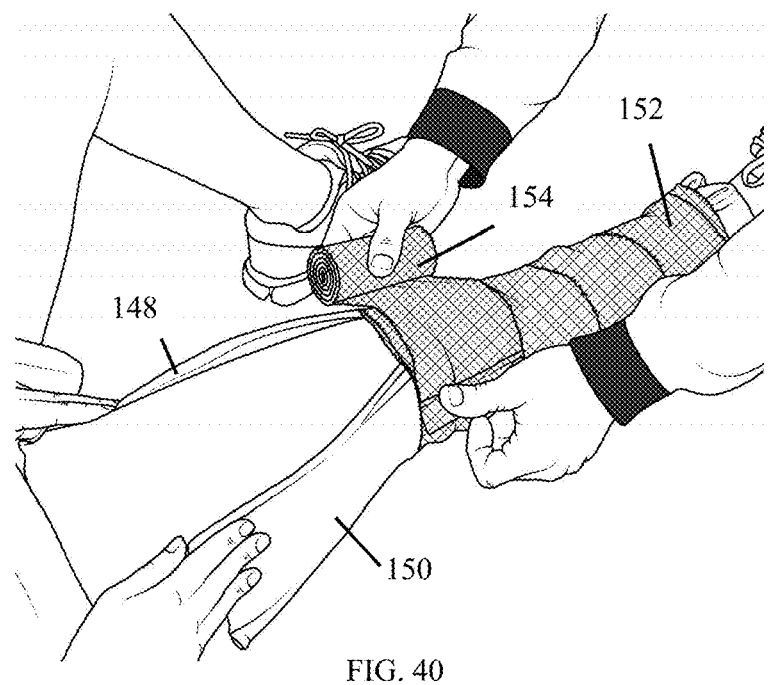
FIG. 40 is an environmental view thereof.
Figure 41:
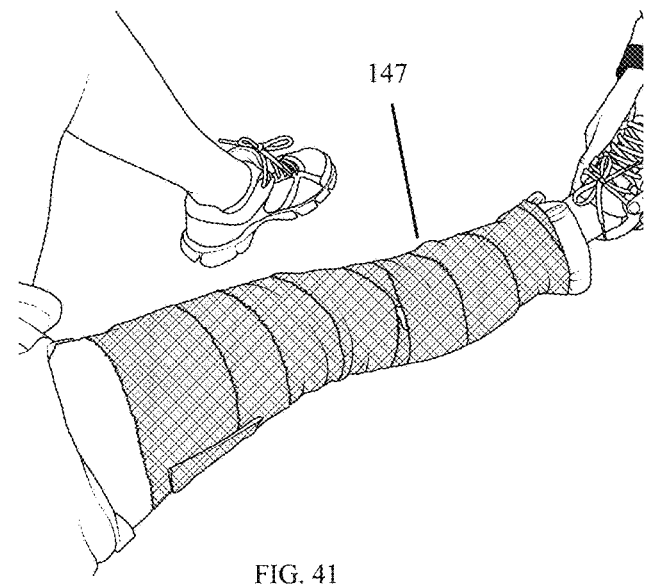
FIG. 41 is an environmental view thereof.
Figure 42:
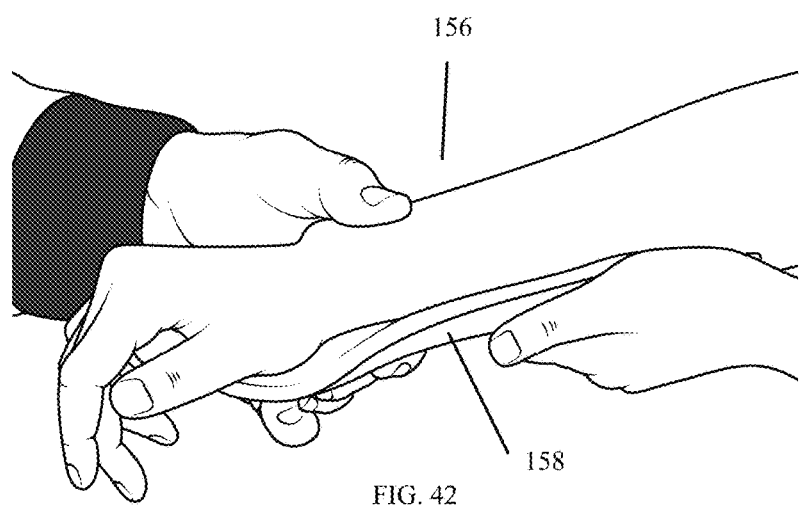
FIG. 42 is an environmental view of one embodiment of the present invention.
Figure 43:
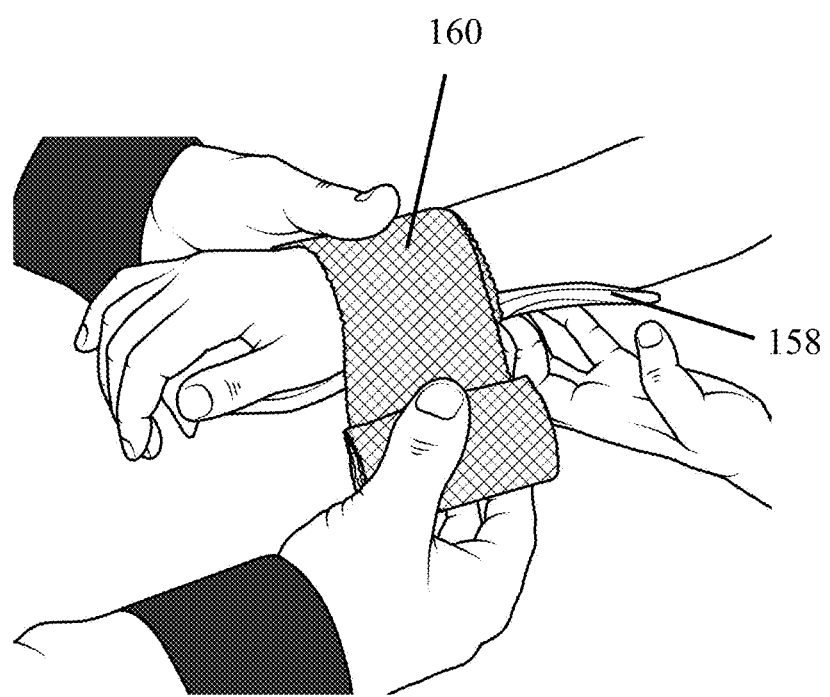
FIG. 43 is an environmental view thereof.
Figure 44:
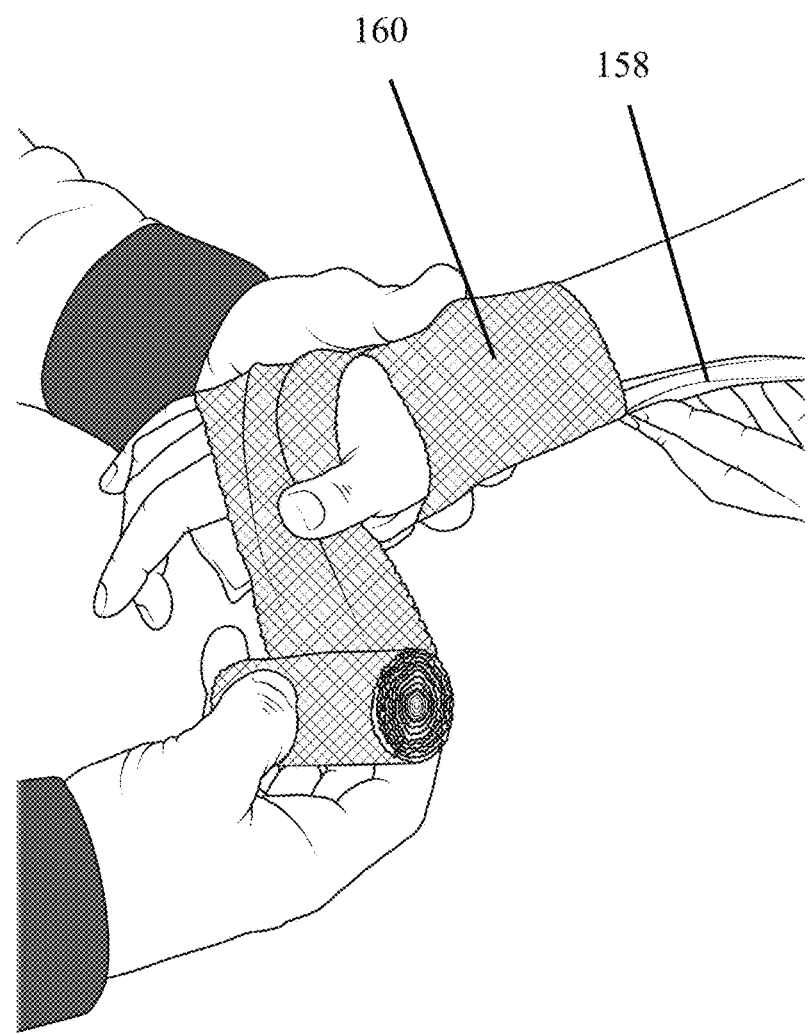
FIG. 44 is an environmental view thereof.
Figure 45:
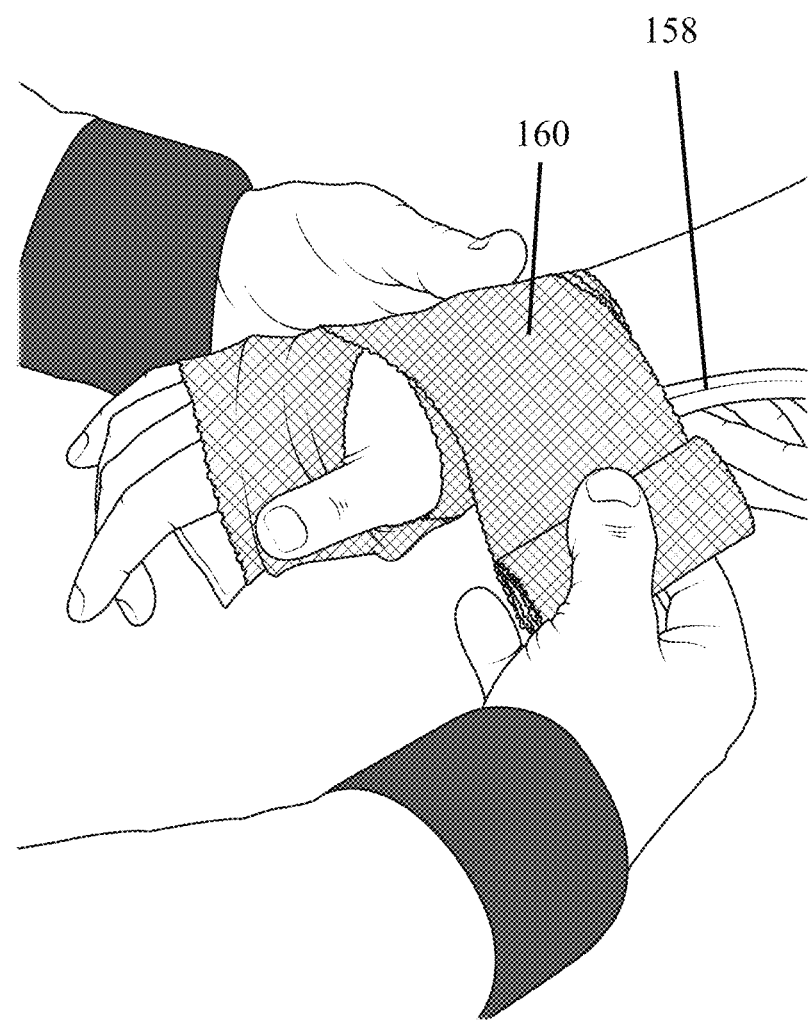
FIG. 45 is an environmental view thereof.
Figure 46:
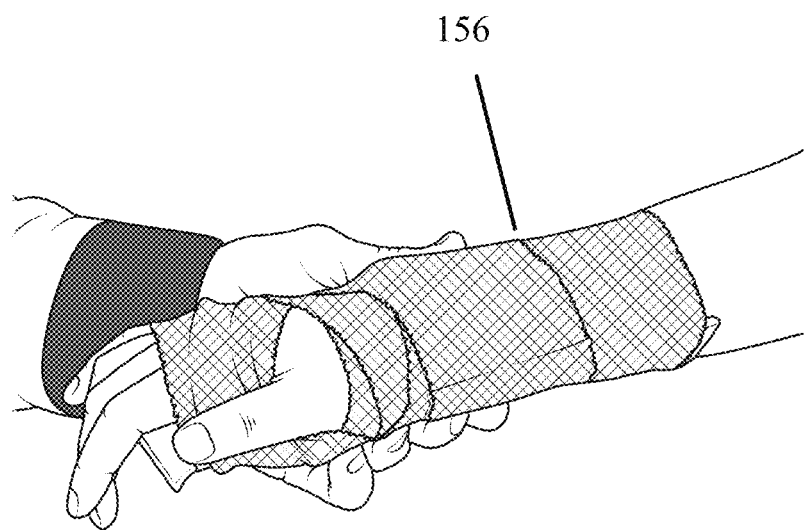
FIG. 46 is an environmental view thereof.

FIGS. 34-36 show the splint 144 and bandage 146 of forearm splint kit 143, also called a sugar tong. The forearm splint kit 143 is available in both a child size and an adult size.

The splint 144 of the child size forearm splint kit ranges from one half (½) inch wide to four (4) inches wide, preferably two (2) inches wide. The length of the splint 144 may range from fifteen (15) inches to fifty (50) inches, preferably twenty-six (26) inches. The bandages 146 of the child size forearm splint kit ranges from one (1) to eight (8) inches in width, preferably three (3) inches.

The splint 144 of the adult size forearm kit ranges from two (2) inches wide to six (6) inches wide, preferably three (3) inches wide. The length of the splint 144 may range from ten (10) inches to fifty (50) inches, preferably thirty six (36) inches. The bandages 146 of the adult size forearm kit ranges from two (2) to ten (10) inches in width, preferably four (4) inches.

FIGS. 34-36 also show the instructions for applying the forearm splint kit 143. These instructions may be provided on the housing 101 at instructions 108. FIGS. 34-36 show the placement of the splints 144 on the arm and elbow of the user for setting the splint.

FIGS. 37-41 show the splints 148, 150 and bandages 152, 154 of knee splint kit 147. The knee splint kit 147 provides a first splint 148 and a second splint 150. The knee splint kit 147 also provides a first bandage 152 and a second bandage 154. The ankle splint kit 147 is available in both a child size and an adult size.

The splints 148, 150 of the child size knee kit range from two (2) inches wide to eight (8) inches wide, preferably four (4) inches wide. The length of the splints 148, 150 may range from ten (10) inches to thirty (30) inches, preferably sixteen (16) inches. The bandages 152, 154 of the child size knee kit range from two (2) to ten (10) inches in width, preferably four (4) inches.

The splints 148, 150 of the adult size knee kit ranges from two (2) inches wide to ten (10) inches wide, preferably five (5) inches wide. The length of the splints 148, 150 may range from ten (10) inches to forty (40) inches, preferably twenty (20) inches. The bandages 152, 154 of the adult size knee kit range from two (2) to twelve (12) inches in width, preferably six (6) inches.

FIGS. 37-41 also show the instructions for applying the knee splint kit 147. These instructions may be provided on the housing 101 at instructions 108. FIGS. 37-41 show the placement of the splints 148, 150 on the leg of the user for setting the splint.

FIGS. 42-46 show the splint 158 and bandage 160 of wrist splint kit 156. The wrist splint kit 156 is available in both a child size and an adult size.

The splint 158 of the child size wrist splint kit ranges from one half (½) inch wide to six (6) inches wide, preferably three (3) inches wide. The length of the splint 158 may range from five (5) inches to fifteen (15) inches, preferably eight (8) inches. The bandage 160 of the child size wrist splint kit range from one (1) to eight (8) inches in width, preferably three (3) inches.

The splint 158 of the adult size wrist splint kit ranges from one half (½) inch wide to six (6) inches wide, preferably three (3) inches wide. The length of the splint 158 may range from five (5) inches to twenty (20) inches, preferably ten (10) inches. The bandage 160 of the adult size wrist splint kit range from one (1) to eight (8) inches in width, preferably three (3) inches.

FIGS. 42-46 also show the instructions for applying the wrist splint kit 156. These instructions may be provided on the housing 101 at instructions 108. FIGS. 42-46 show the placement of the splint 158 on the arm and wrist of the user for setting the splint.

In one embodiment, such as a kit for use in the doctor's office or other locations where a clean water source is available, the present invention may be packaged without a water source. The kit may also provide a set of scissors for any sizing that the user or caregiver may choose to make.

From the foregoing, it will be seen that the present invention is one well adapted to obtain all the ends and objects herein set forth, together with other advantages which are inherent to the structure.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. A kit for splinting at least one body part of a user, the kit comprising:
   an elastic bandage;
   a first splint that hardens when contacted with moisture, wherein the first splint is sized for a single use application;
   a second splint that hardens when contacted with moisture, wherein the second splint is sized for a single use application;
   a splint housing providing a moisture proof seal around the first splint and the second splint wherein the splint housing stores the first splint and the second splint without sealing the first splint separately from the second splint;
   a fluid container;
   a main housing storing the bandage, the splint housing, the first splint and the second splint, and the fluid container;

wherein the splint housing is configured to be opened along a first opening notch of the splint housing located on a first side of the splint housing near a first end of the splint housing, wherein opening the splint housing along the first opening notch removes at least a portion of the splint housing to create a first opening in the splint housing;

wherein the first opening of the splint housing is configured for applying water into the first opening of the splint housing;

wherein the first opening is configured to be enlarged by opening the splint housing along a second opening notch of the splint housing located on the first side of the splint housing, the first opening notch located between the second opening notch and the first end of the housing along the first side of the splint housing wherein the second opening notch remains on the splint housing after removal of the portion of the splint housing, wherein opening the splint housing along the second opening notch removes an additional portion of the splint housing to enlarge the first opening;

wherein at least one of the splints is configured to be removed from the splint housing through the first opening after water is applied into the splint housing and the first opening is enlarged.

2. The kit of claim 1 wherein the first splint is fully encased within felt at the time of use, the first splint sized for use without cutting the splint.

3. The kit of claim 1 wherein the first splint is fully encased within a foam material at the time of use, the first splint sized for use without cutting the splint.

4. The kit of claim 1 wherein the second splint is sized differently than the first splint.

5. A kit for splinting at least one body part of a user, the kit comprising:
   an elastic bandage;
   a first splint constructed from fiberglass that hardens when contacted with water wherein the fiberglass is fully encased, wherein the first splint is sized for a single use application, the first splint being sized based upon the body part to be splinted and the size of the user;
   a splint housing providing a moisture proof seal around the splint wherein the splint is stored within the splint housing;
   a sealed fluid container at least partially filled with water; and
   a main housing storing the bandage, the splint housing, the first splint, and the fluid container;

wherein the splint housing is configured to be opened along a first opening notch of the splint housing located on a first side of the splint housing near a first end of the splint housing, wherein opening the splint housing along the first opening notch removes at least a portion of the splint housing to create a first opening in the splint housing;

wherein the water is configured to be applied from the sealed fluid container into the first opening of the splint housing;

wherein the splint housing is configured to be agitated with the water in the splint housing;

wherein the first opening is configured to be enlarged after applying water into the splint housing wherein the first opening is enlarged by opening the splint housing along a second opening notch of the splint housing located on the first side of the splint housing, the first opening notch located between the second opening notch and the first end of the housing along the first side of the splint housing wherein the second opening notch remains on the splint housing after removal of the portion of the splint housing, wherein opening at the second opening notch removes an additional portion of the splint housing to enlarge the first opening;

wherein the splint is configured to be removed from the splint housing through the first opening after the first opening is enlarged.

6. The kit of claim 1 wherein water applied into the splint housing contacts both the first splint and the second splint to harden the first splint and the second splint.

\* \* \* \* \*